United States Patent [19]
Dustrude et al.

[11] Patent Number: 5,911,752
[45] Date of Patent: Jun. 15, 1999

[54] METHOD FOR COLLAPSING A STENT

[75] Inventors: Mark Owen Dustrude, Minnetonka; James V. Donadio, III, Chaska; J. Edward Shapland, II, Shoreview, all of Minn.

[73] Assignee: IntraTherapeutics, Inc., St. Paul, Minn.

[21] Appl. No.: 08/710,245

[22] Filed: Sep. 13, 1996

[51] Int. Cl.⁶ ...................................................... A61F 2/06
[52] U.S. Cl. .............................. 623/1; 606/191; 606/195; 606/198; 606/192; 604/96
[58] Field of Search ................................. 623/1, 11, 12; 604/96, 104; 606/153–156, 108, 190–200; 128/898

[56] References Cited

U.S. PATENT DOCUMENTS

| | | |
|---|---|---|
| 3,657,744 | 4/1972 | Ersek . |
| 4,553,545 | 11/1985 | Maass et al. . |
| 4,733,665 | 3/1988 | Palmaz . |
| 4,739,762 | 4/1988 | Palmaz . |
| 4,776,337 | 10/1988 | Palmaz . |
| 4,793,348 | 12/1988 | Palmaz . |
| 4,856,516 | 8/1989 | Hillstead . |
| 4,893,623 | 1/1990 | Rosenbluth . |
| 4,994,071 | 2/1991 | MacGregor . |
| 5,102,417 | 4/1992 | Palmaz . |
| 5,135,536 | 8/1992 | Hillstead . |
| 5,195,984 | 3/1993 | Schatz . |
| 5,197,978 | 3/1993 | Hess . |
| 5,266,073 | 11/1993 | Wall . |
| 5,306,294 | 4/1994 | Winston et al. . |
| 5,342,348 | 8/1994 | Kaplan . |
| 5,344,426 | 9/1994 | Lau et al. . |
| 5,354,309 | 10/1994 | Schnepp-Pesch et al. . |
| 5,366,473 | 11/1994 | Winston et al. . |
| 5,382,261 | 1/1995 | Palmaz . |
| 5,383,892 | 1/1995 | Cardon et al. . |
| 5,419,760 | 5/1995 | Narciso, Jr. . |
| 5,423,885 | 6/1995 | Williams . |
| 5,449,373 | 9/1995 | Pinchasik et al. . |
| 5,514,154 | 5/1996 | Lau et al. . |
| 5,634,928 | 6/1997 | Fischell et al. .......................... 606/108 |
| 5,653,691 | 8/1997 | Rupp et al. ............................... 604/96 |
| 5,658,309 | 8/1997 | Berthiaume et al. ..................... 604/96 |

FOREIGN PATENT DOCUMENTS

| | | |
|---|---|---|
| 0 364 787 | 4/1990 | European Pat. Off. . |
| 0 423 916 A1 | 4/1991 | European Pat. Off. . |
| WO 92/09246 | 6/1992 | WIPO . |
| WO 94/20044 | 9/1994 | WIPO . |
| WO 95/30385 | 11/1995 | WIPO . |

*Primary Examiner*—Mickey Yu
*Assistant Examiner*—Francis K. Cuddihy
*Attorney, Agent, or Firm*—Merchant, Gould, Smith, Edell, Welter & Schmidt

[57] ABSTRACT

A method for implanting a stent within a body passageway defined by a body wall. The method includes the step of fabricating the stent in an initial orientation in which the stent has an initial diameter and an initial length. The method also includes the step of collapsing the stent radially inward from the initial orientation to a collapsed orientation in which the stent has a collapsed length and a collapsed diameter. The stent is collapsed by deforming a portion of the stent beyond the elastic limit of the portion of the stent. The method further includes the step of positioning the collapsed stent at a desired location within the body passageway. Additionally, the method includes the step of expanding the stent radially outward from the collapsed orientation to a deployed orientation in which the stent has a deployed diameter and a deployed length. The deployed diameter and the deployed length are respectively substantially equal to the initial diameter and the initial length. The stent is expanding by deforming the portion of the stent beyond the elastic limit of the portion of the stent.

6 Claims, 11 Drawing Sheets

METHOD FOR COLLAPSING A STENT

FIELD OF THE INVENTION

The present invention relates generally to expandable vascular grafts for use within body passageways. More particularly, the present invention relates to expandable stents for maintaining the patency of blood vessels and to a method for implanting such expandable stents within a body passageway.

BACKGROUND OF THE INVENTION

Stents are commonly used to provide mechanical reinforcement for maintaining the patency of body passageways and cavities. Exemplary body passageways include blood vessels, the urethra, the bile duct, the esophagus, and the ureters.

A common use for stents is in the treatment of coronary artery disease. Coronary artery disease involves the narrowing or constricting of a coronary artery such that blood flow through the artery is diminished. Such a situation is commonly treated by balloon angioplasty procedures in which the afflicted artery is dilated/expanded through use of a balloon catheter. Without artificial reinforcement, the balloon expanded vessel has a tendency to constrict back to its previous obstructed internal diameter shortly after an angioplasty procedure. By implanting a stent along the expanded portion of the vessel, the vessel is provided with sufficient radial reinforcement to prevent the vessel from constricting.

Besides preventing vessel constriction, stents provide another important function when used in association with balloon angioplasty procedures. During a typical balloon angioplasty procedure, it is common for the afflicted artery to split or tear as it is expanded. The tearing of the vessel produces flaps of tissue that may project into the lumen of the vessel thereby interfering with blood flow. To prevent the aforementioned problem, a stent is implanted at the obstruction/constriction location. The stent compresses the flaps against the vessel to prevent interference with blood flow and to prevent the flaps from tearing from the vessel and entering the blood stream.

A variety of stent designs are known in the prior art. One category of stent design relates to self-expanding stents. Two types of self-expanding stents are prevalent in the medical field. The first type of self-expanding stent is fabricated of highly elastic material and exhibits elastic spring back characteristics. A common elastic self-expanding stent configuration comprises a helical stainless steel spring. The second type of self-expanding stent relates to temperature sensitive stents. Such temperature sensitive stents expand or contract in a radial direction depending upon their temperature.

An elastic self-expanding stent is typically manufactured in an enlarged orientation such that the stent has an enlarged diameter. The elastic self-expanding stent is then compressed to a compressed orientation in which the stent has a diameter sufficiently small to be inserted in a vessel. Once the stent is compressed to the compressed orientation, the stent is inserted within or on a catheter body that exerts sufficient radial stress upon the stent to prevent the stent from expanding. After the stent has been directed via the catheter to a desired location within a vessel, the elastic self-expanding stent is disengaged from the catheter. Upon disengagement from the catheter the radial compressive force provided by the catheter is removed and the stent automatically expands, via its elastic construction, from the compressed orientation to the expanded orientation. In the expanded orientation, the stent radially engages the vessel such that the vessel is reinforced to maintain the patency of the vessel. Additionally, contact between the vessel and the stent prevents the stent from migrating within the vessel.

A problem with elastic self-expanding stents is that they typically experience substantial length variations when transitioning between the compressed and expanded orientations. The significant length variation associated with such elastic self-expanding stents makes it difficult to precisely place the stents at a particular location within a body.

A temperature sensitive self-expanding stent is typically manufactured of a two-way shape-memory alloy such as Nitinol. Such a stent is designed to have an expanded orientation when the stent has a temperature above a shape transition temperature which is typically above room temperature and may be equal to body temperature. The temperature sensitive stent is radially compressed to a constricted orientation for implantation in a body vessel via a catheter. Once the stent is positioned at a desired location in the vessel, heat absorbed from the body causes the stent to expand to the expanded configuration. In the expanded configuration, the stent engages the vessel such that the vessel is radially reinforced.

Another category of stent relates to non-self-expanding stents. An exemplary non-self-expanding stent is disclosed in U.S. Pat. No. 4,733,665. Such stents typically are constructed of a deformable material. The deformable material allows the stents to maintain their shape when expanded. The stents are typically pre-equipped with a manufacturing installed catheter balloon and are typically manufactured with a small diameter sized to permit insertion into a vessel.

In use, a physician directs a non-self-expanding stent, via a catheter, to a desired location within a vessel. Once the stent reaches the desired location, the physician inflates the balloon in a controlled manner such that the stent is caused to expand. As the stent is expanded, the deformable material used to construct the stent deforms beyond its elastic limit. Consequently, the expanded stent has a tendency to maintain its expanded shape. Once expanded, the stent reinforces the vessel by providing radial reinforcement for maintaining the patency of the vessel.

A problem with a conventional non-self-expanding stent is that stress generated by a vessel in which the stent is implanted can cause the stent to be compressed radially inward thereby reducing the lumen size of the vessel. One reason for this problem is that when the non-self-expanding stent is expanded/deformed from a small diameter to an enlarged diameter, the individual members forming the stent have a tendency to twist relative to one another. The relative twisting of the members affects the structural integrity of the stent thereby reducing the stent's ability to resist vessel pressure.

SUMMARY OF THE INVENTION

The present invention relates to a method for implanting a stent within a body passageway. The method includes the step of fabricating the stent in an initial fabrication orientation. In the initial fabrication orientation, the stent has an initial fabrication diameter and an initial fabrication length. The stent is fabricated to have a predetermined flexibility and a radial reinforcement strength.

After the stent is fabricated in the initial fabrication orientation, the stent is collapsed radially inward by deforming a portion of the stent beyond the elastic limit of the portion of stent. The collapsed stent has a collapsed diameter and a collapsed length. The collapsed diameter is sized to allow the stent to be inserted into the body passageway.

After the stent is collapsed, the stent is positioned at a desired location within the body passageway. When the stent is positioned at the desired location within the body passageway, the stent is expanded radially outward to a deployed orientation by deforming portions of the stent beyond their elastic limits. In the deployed orientation, the stent contacts the body passageway and has a deployed diameter and a deployed length that are respectively substantially equal to the initial fabrication diameter and the initial fabrication length.

It is significant that the deployed diameter and the deployed length are respectively substantially equal to the initial fabrication diameter and the initial fabrication length. Such a feature provides numerous advantages. For example, the similarities of the fabrication orientation and the deployed orientation facilitate a physician's ability to select a stent of suitable diameter and length for a given use. Also, by providing the physician with the stent in the fabricated orientation, the physician can collapse the stent radially inward upon his or her own catheter balloon rather than being forced to utilize a balloon installed within the stent during the manufacturing process. Furthermore, because the deployment diameter and the deployment length are respectively substantially equal to the initial fabrication diameter and the initial fabrication length, there is minimal twisting of the individual members that form the stent when the stent is actually implanted in the patient. Consequently, the deployed stent and the initially fabricated stent demonstrate similar flexibility and reinforcement strength characteristics.

Another aspect of the present invention relates to a method for collapsing a stent. The method includes the step of providing a stent having an expanded orientation. Next, a catheter balloon is placed within the stent. Finally, centripetally directed radial forces are applied substantially uniformly about the perimeter of the stent. The radial forces are of sufficient magnitude to deform portions of the stent beyond their elastic limits such that the stent collapses radially inward from the expanded orientation to a collapsed orientation. In the collapsed orientation, the stent is compressed upon the balloon and sized for insertion within a body passageway.

Another aspect of the present invention relates to a method for fabricating a stent. Generally, the method includes the step of first providing a solid tube member having an initial expanded diameter. The initial expanded diameter is substantially equal to a final expanded diameter which the tube member is intended to have when implanted in a body. A plurality of apertures are then cut within the tube member while tube member maintains its initial expanded diameter.

A further aspect of the present invention relates to a stent including a tubular stent body moveable between an expanded orientation and a collapsed orientation. A plurality of apertures are cut within the stent body. The apertures are defined by a plurality of contiguous non-overlapping strut members. In certain embodiments, all of the strut members have axial components that are substantially parallel to a longitudinal axis of the tubular stent body to facilitate collapsing the stent. Portions of the strut members are constructed and arranged to be deformed beyond their elastic limits when the stent body is moved between the expanded and collapsed orientations.

A variety of additional advantages of the invention will be set forth in part in the description which follows, and in part will be obvious from the description, or may be learned by practice of the invention. The advantages of the invention will be realized and attained by means of the elements and combinations particularly pointed out in the claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the invention and together with the description, serve to explain the principles of the invention. A brief description of the drawings is as follows:

FIG. 1b shows a schematic side view of the initially fabricated stent of FIG. 1a;

DETAILED DESCRIPTION OF THE PREFERRED EMBODIMENT

Reference will now be made in detail to exemplary embodiments of the present invention which are illustrated in the accompanying drawings. Wherever possible, the same reference numbers will be used throughout the drawings to refer to the same or like parts.

Figure 1A:
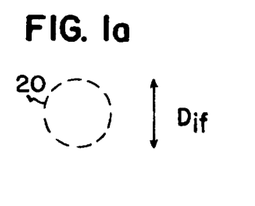
FIG. 1a shows a schematic end view of a stent as initially fabricated.
Figure 1B:
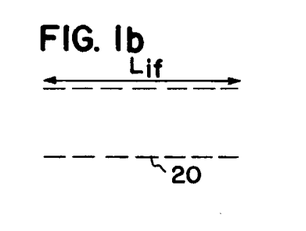

FIGS. 1a–1h illustrate a method for implanting a stent in accordance with the principles of the present invention. FIGS. 1a and 1b show a stent 20 in an initial fabrication orientation. In the initial fabrication orientation, the stent 20 has an initial fabrication diameter $D_{if}$ and an initial fabrication length $L_{if}$. The initial fabrication diameter $D_{if}$ and the initial fabrication length $L_{if}$ are preferably equal to the intended use diameter and the intended use length of the stent 20.

It will be appreciated that the stent 20 preferably has a tubular shape and is constructed to have a predetermined flexibility and a predetermined radial reinforcement strength. Radial reinforcement strength and flexibility are determinable physical characteristics that are dependent upon the structural design of the stent 20. The stent 20 is preferably made from a biocompatible material having elasticity characteristics that allow the stent 20 to be expanded and collapsed. The material must be sufficiently deformable to permit the stent to retain its expanded and collapsed orientations. Suitable materials for fabrication of the stent would include silver, tantalum, stainless steel, gold, titanium, Nitinol or any suitable plastic material.

It will be appreciated that the stent 20 could be constructed from a plurality of overlapping/intertwined wire members configured to form an elongated tube, the wire members being interconnected at the points at which the wire members overlap one another. Alternatively, the stent 20 could comprise a tube having a pattern cut therein via a conventionally known cutting process. Exemplary cutting processes include stamping, electromechanical cutting, laser cutting, and chemical etching. An exemplary chemical etching process suitable for manufacturing a stent having an initial fabrication diameter equal to the intended use/final expanded diameter of the stent is described later in the specification with respect to FIG. 6.

Figure 1C:
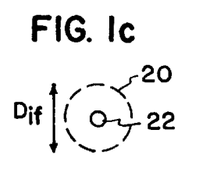
FIG. 1c shows an end view of the stent of FIG. 1a with a catheter inserted therein.
Figure 1D:
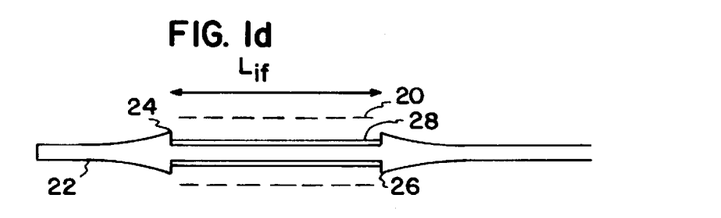
FIG. 1d shows a schematic side view of the stent of FIG. 1a with a catheter inserted therein.

FIGS. 1c and 1d show the stent 20 in the initial fabrication orientation with a conventional balloon catheter 22 inserted therein. The balloon catheter 22 includes distal and proximal retaining structures 24 and 26 for retaining the stent 20 on the catheter 22. The catheter 22 also includes a balloon 28 for expanding the stent 20.

Figure 1E:
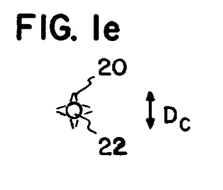
FIG. 1e shows a schematic end view of the stent of FIG. 1a compressed upon a catheter.
Figure 1F:
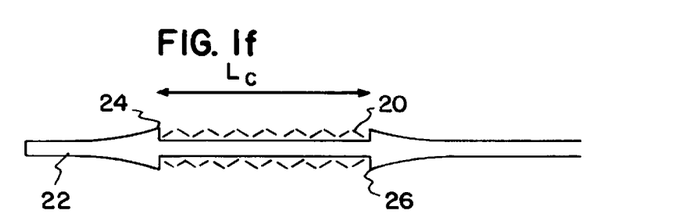
FIG. 1f shows a schematic side view of the stent of FIG. 1a compressed upon a catheter.

FIGS. 1e and 1f illustrate the stent 20 in a collapsed orientation. The stent 20 is shown collapsed radially inward upon the catheter 22. In the collapsed orientation, the stent 20 has a collapsed diameter $D_c$ that is sufficiently small to allow the stent 20 and the catheter 22 to be inserted within a desired body passageway. Additionally, it will be appreciated that as stent 20 is collapsed radially inward, the stent 20 elongates to a collapsed length $L_c$ that is longer than the initial fabrication length $L_{if}$. However, in certain embodiments, the length $L_c$ may be equal to the length $L_{if}$. As collapsed, the stent 20 is firmly retained on the catheter 22, or within a sleeve on the catheter 22, thereby allowing the stent 20 to be safely inserted within a body.

It will be appreciated that the stent 20 can be collapsed by a variety of techniques. Specific exemplary collapsing techniques are described later in the specification. However, generally, the stent 20 is collapsed by exerting centripetally directed forces uniformly about the circumference of the stent 20. The forces cause the stent to deform radially inward. The forces are preferably great enough to cause at least portions of the stent 20 to deform beyond their elastic limits. By deforming portions of the stent 20 beyond their elastic limits, the stent 20 will retain its collapsed orientation even after the collapsing forces are no longer applied to the stent 20.

Throughout the specification, references are made to deforming portions of the stent beyond their elastic limits. Such references are intended to mean that the portions of the stent are sufficiently deformed so as to demonstrate plastic/inelastic characteristics such that the stent substantially maintains the deformed position.

Figure 1G:
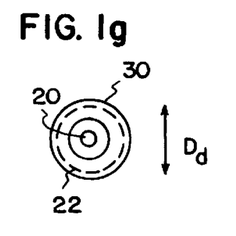
FIG. 1g shows a schematic end view of the stent of FIG. 1a expanded within a body passageway.
Figure 1H:
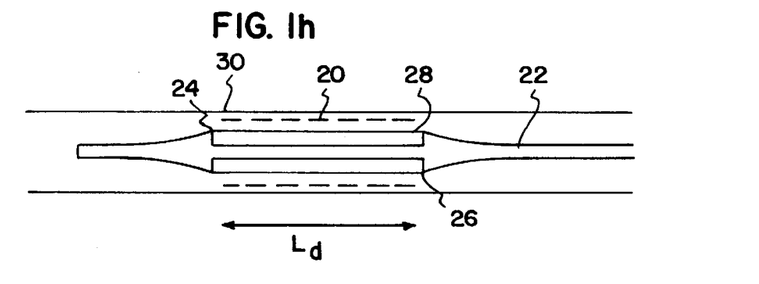
FIG. 1h shows a schematic side view of the stent of FIG. 1a expanded within a body passageway.

FIGS. 1g and 1h illustrate the stent 20 in a deployed orientation. The stent 20 is shown implanted within an exemplary body passageway 30. In the deployed orientation the stent 20 has a diameter $D_d$ that is substantially equal to the initial fabrication diameter $D_{if}$. Also, when the stent 20 is in the deployed orientation, the stent 20 has a deployment length $L_d$ that is substantially equal to the initial fabrication length $L_{if}$. Consequently, when the stent 20 is in the deployed orientation, the stent 20 has substantially the same structural configuration as when it was initially fabricated and there is very little twisting between the individual members that form the stent 20. It will be appreciated that the stent 20 as implanted within the body 30 demonstrates similar physical characteristics such as reinforcement strength and flexibility as the stent at the initial fabrication stage.

The stent 20 is deployed within the body passageway 30 by positioning the stent 20 at a desired location within the body passageway 30 via the catheter 22. Once the stent 20 is at the desired location within the body passageway 30, the catheter balloon 28 is inflated causing a controlled radial expansion of the stent 20. The balloon 28 preferably exerts sufficient force against the stent 20 to cause portions of the stent 20 to deform beyond their elastic limits. Because portions of the stent 20 are expanded beyond their elastic limits, the stent 20 will maintain its expanded state within the body vessel 30. Once the stent 20 is expanded, the catheter 22 can be removed from the body passageway 30.

Figure 2A:
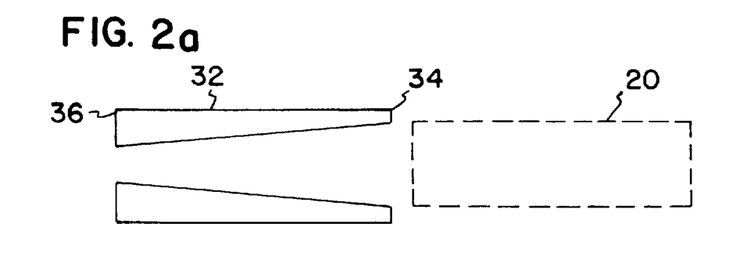
FIG. 2a schematically shows a stent prior to being forced through a tube having a tapered inner diameter.
Figure 2B:
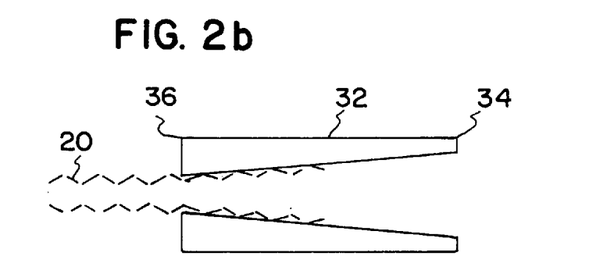
FIG. 2b shows the stent in the process of being forced through the tube having the tapered inner diameter.
Figure 2C:
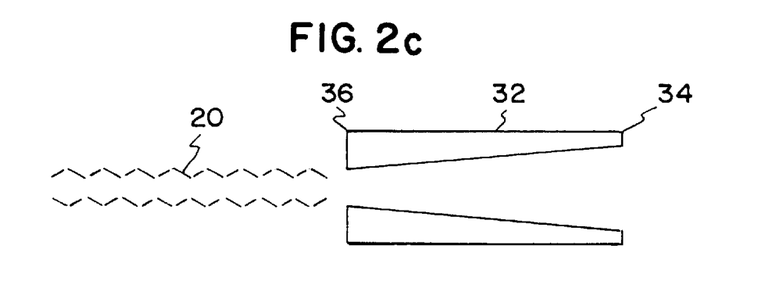
FIG. 2c shows the stent after having been forced through the tube having the tapered inner diameter.

FIGS. 2a–2c illustrate one method for collapsing the stent 20. The method involves forcing the stent 20 longitudinally through a tube 32 having a tapered inner diameter. The tube 32 has an inlet end 34 having an enlarged inlet diameter and an outlet end 36 having a constricted outlet diameter. To collapse the stent 20, one end of the stent 20 is inserted into the inlet end 34 of the tube 32. The stent 20 is then forced through the tube 32 toward the outlet end 36. As the stent 20 is forced through the tube 32, the tapering inner diameter of the tube 32 compresses the stent 20 (as best shown in FIG. 2b). The compression of the stent 20 by the inner diameter of the tube 32 causes at least portions of the stent 20 to deform beyond their elastic limits. Once the entire stent 20 is forced through the tube 32, the entire stent 20 has an outer diameter approximately equal to the constricted inner diameter of the outlet end 36 of the tube 32.

Figure 3A:
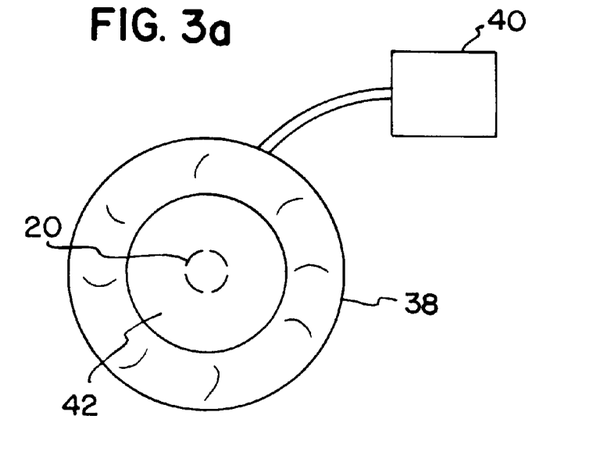
FIG. 3a shows an end view of a stent placed within an inflatable cuff, the cuff is in a non-inflated state.
Figure 3B:
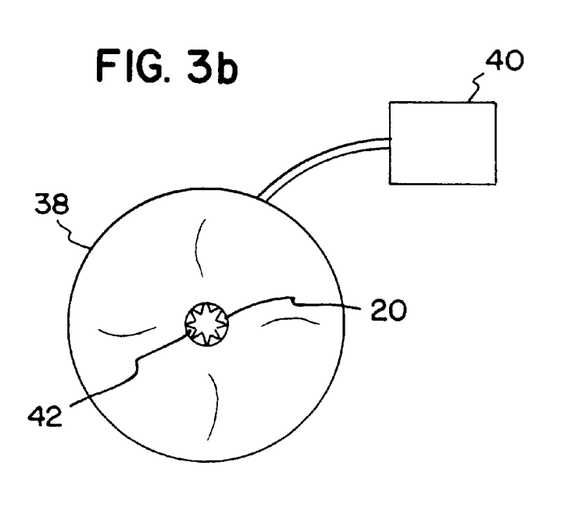
FIG. 3b shows an end view of the stent being compressed by the inflatable cuff, the cuff is shown in an inflated state.

FIGS. 3a and 3b illustrate another method for collapsing the stent 20. The method utilizes an inflatable cuff 38 selectively in fluid communication with a source of compressed fluid 40 (liquid or gas). The cuff 38 is generally cylindrical and defines an inner opening 42 extending longitudinally through the cuff 38. To compress the stent 20, the inflatable cuff 38 is first deflated such that the inner opening 42 enlarges. The stent 20 is then inserted within the enlarged inner opening 42 of the inflatable cuff 38. Once the stent 20 is inserted within the cuff 38, the cuff 38 is inflated via the source of compressed air 40. As the cuff 38 inflates, the inner opening 42 of the cuff 38 constricts such that the cuff 38 exerts centripetally directed radial forces about the circumference of the stent 20. The forces cause the stent 20 to deform radially inward such that portions of the stent 20 are deformed beyond their elastic limits. Because portions of the stent 20 are deformed beyond their elastic limits, the stent 20 will maintain its collapsed orientation even after the cuff 38 has been removed from the exterior of the stent 20. The cuff is removed from the exterior of the stent 20 by deflating the cuff 38 such that the inner opening 42 enlarges to provide clearance for removing the stent 20 therefrom.

Figure 4A:
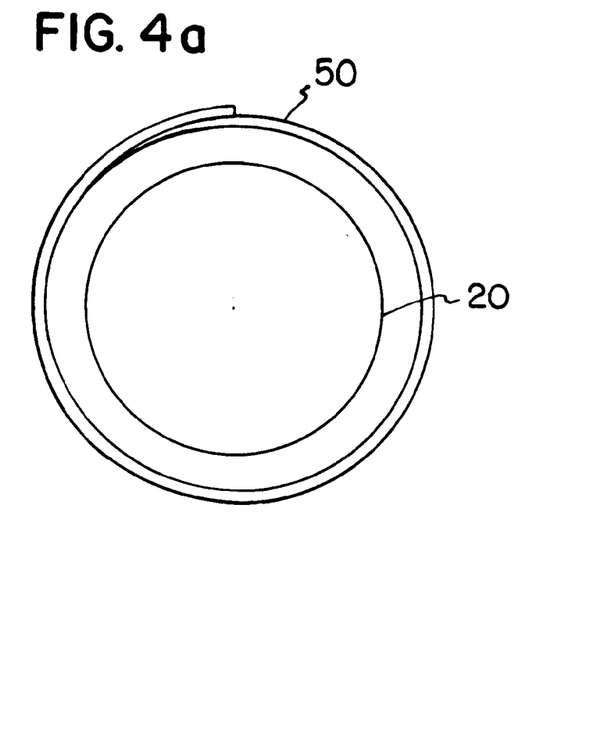
FIG. 4a shows an end view of a stent placed within a mechanical sleeve, the sleeve is in an expanded orientation.
Figure 4B:
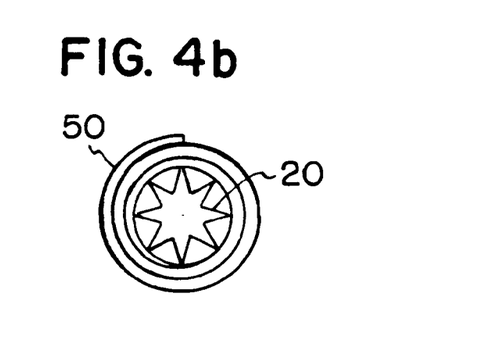
FIG. 4b shows an end view of the mechanical cuff in a constricted orientation.

FIGS. 4a and 4b illustrate another method for collapsing the stent 20. The method employs a mechanical compression sleeve 50 comprising a substantially flat member that is rolled upon itself to form a generally cylindrical tube. It will be appreciated that the longitudinal ends of the flat member are overlapped such that the sleeve 50 defines an inner longitudinal opening sized to receive the stent 20. To collapse the stent 20, the stent 20 is first placed in the sleeve 50 as shown in FIG. 4a. Next, the sleeve 50 is rolled further upon itself causing greater overlap between the ends of the flat member such that the inner diameter of the sleeve 50 constricts as shown in FIG. 4b. As the inner diameter of the sleeve 50 constricts, the stent 20 is deformed radially inward from the expanded orientation to the collapsed orientation.

It will be appreciated that a variety of tensioning means can be utilized to roll the sleeve 50 upon itself. For example, a belt equipped with a ratchet mechanism can be wrapped around the exterior of the sleeve for compressing the sleeve 50. Alternatively, a structure similar to a hose clamp can be wrapped around the exterior of the sleeve 50 and tensioned to constrict the sleeve. A conventional hose clamp structure typically comprises a strap member that has overlapping ends. The strap member has a plurality of transverse slots. A threaded member is rotatably mounted at one of the ends of the strap member. The threaded member is longitudinally aligned with the strap member and the threads of the threaded member cooperate with the slots in the strap member. By rotating the threaded member, the diameter of the loop formed by the strap member is varied.

FIGS. 5a–5d illustrate another method for collapsing the stent 20. The method utilizes a split collet mechanism 60. The split collet mechanism 60 includes a cylindrical outer sleeve 62 having a tapered inner diameter. An inner sleeve structure 63 including a plurality of collet members 64 is reciprocally mounted within the outer sleeve 62. The collet members 64 have radially curved inner surfaces 66 that cooperate to form a cylindrical inner opening of the inner sleeve 63. The collet members 64 also have radially curved outer surfaces 68 that cooperate to define a tapered outer boundary of the inner sleeve 63. The outer taper of the inner sleeve 63 matches the inner taper of the outer sleeve 62. When the inner sleeve 63 is pulled longitudinally outward from the outer sleeve 62, radial spaces are generated between the individual collet members 62 such that the inner opening of the inner sleeve 63 expands. By contrast, when the inner sleeve 63 is pushed longitudinally into the outer sleeve 62, the collet members 64 are pushed radially together such that the radial spaces between the collet members 64 are closed and the inner opening of the inner sleeve 63 constricts.

Figure 5A:
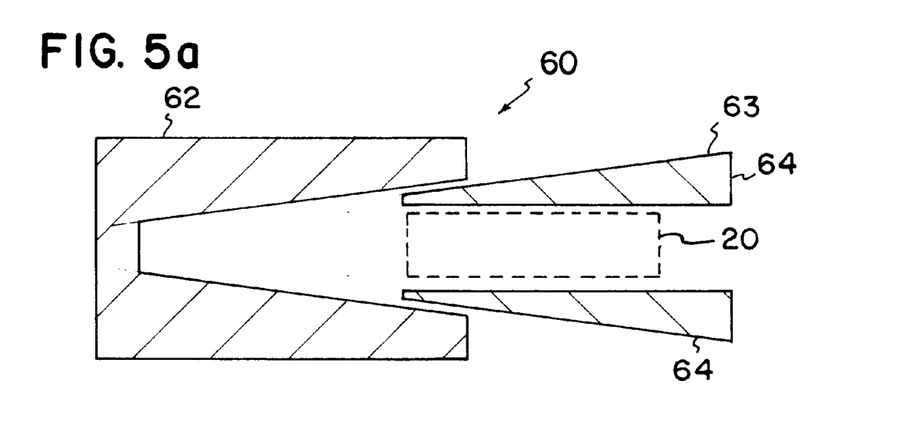
FIG. 5a shows a side cross-sectional view of a split collet mechanism for compressing a stent, the split collet mechanism is shown in an expanded orientation.
Figure 5B:
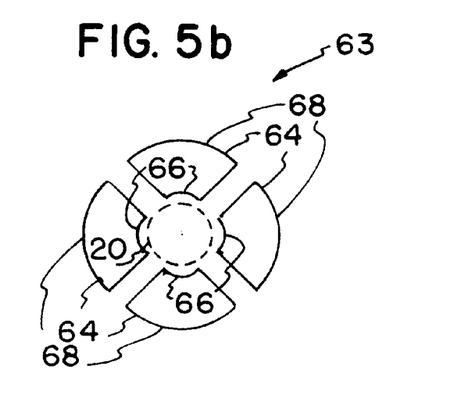
FIG. 5b shows an end view of an inner sleeve that is incorporated within the split collet mechanism of FIG. 5a, the inner sleeve is shown in an expanded orientation.
Figure 5C:
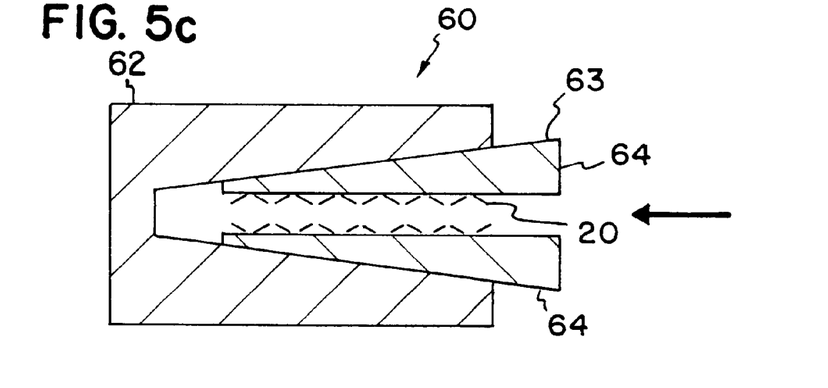
FIG. 5c shows a side cross-sectional view of the split collet mechanism of FIG. 5a in a constricted orientation.
Figure 5D:
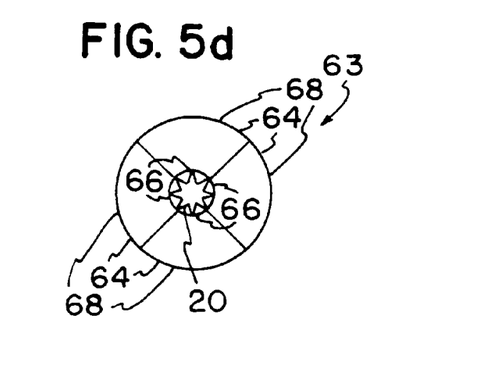
FIG. 5d shows an end view of the inner sleeve of FIG. 5b, the inner sleeve is shown in a constricted orientation.

To collapse the stent 20 using the collet mechanism 60, the stent 20 is placed in the inner opening of the inner sleeve 63 while the inner sleeve 63 is expanded (as shown in FIGS. 5a and 5b). Once the stent 20 is within the expanded inner sleeve 63, the inner sleeve 63 is pushed longitudinally into the outer sleeve 64 causing the stent 20 to be radially compressed and collapsed within the inner opening of the inner sleeve 63 (as shown in FIGS. 5c and 5d).

It will be appreciated that the stent 20 can be collapsed by techniques other than those specifically disclosed. For example, the stent 20 can be collapsed by applying opposing longitudinal forces to opposite ends of the stent 20 such that the stent 20 is stretched. Alternatively, the stent 20 can be collapsed by applying torque to the stent 20 such that the stent 20 is twisted into a collapsed state. Also, it will be appreciated that any of the aforementioned stent collapsing structures can be sold in a kit that includes one or more stents configured to be collapsed by the corresponding collapsing structure. Furthermore, the type of collapsing technique utilized will depend upon the inherent structure of the stent being collapsed. Consequently, particular collapsing techniques will be tailored to particular stent designs.

It will be appreciated that the stent 20 need not be collapsed upon the catheter 22 at the time the stent 20 is manufactured. Instead, the stent 20 could be shipped and sold while in the initial fabricated orientation. In this manner, the stent 20 could be provided to physicians in the initial fabricated orientation. By providing physicians with such a stent 20, the physician's ability to select a stent of the appropriate size for a desired use is enhanced. This is because the initially fabricated diameter and length are substantially the same as the deployed diameter and length. Furthermore, because the stent 20 would be shipped in the initial fabrication orientation, the physician can insert his or her own catheter balloon 28 within the stent 20. After inserting the catheter balloon 28 within the stent 20, the physician would personally collapse the stent 20 on the catheter 22 prior to insertion within the body 30.

It will also be appreciated that the stent can be partially pre-collapsed at the manufacturing facility prior to shipping. The stent 20 would be shipped in the partially collapsed orientation. In the partially collapsed orientation, the inner diameter of the stent 20 is sufficiently large to allow physicians to insert their preferred balloon with the stent 20. Because the stent 20 is partially pre-collapsed, the final collapsing step is made easier.

Figure 6:
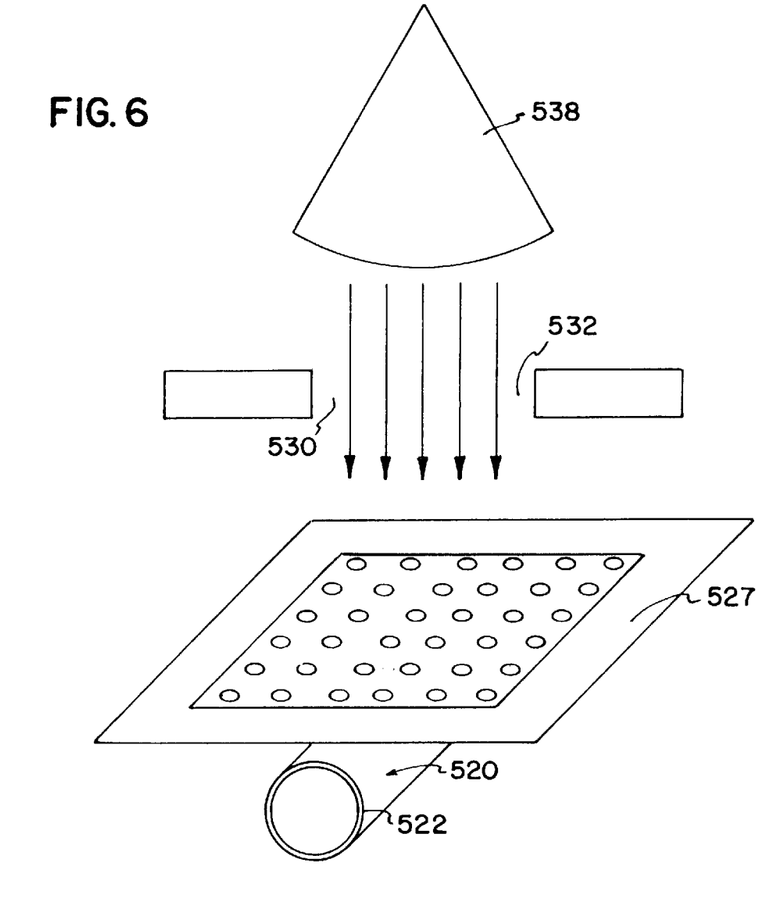
FIG. 6 is a diagrammatic illustration showing an etching method suitable for making stents in accordance with the principles of the present invention.

FIG. 6 shows an exemplary etching process suitable for manufacturing a stent having an initial fabrication diameter that is substantially equal to a final expanded diameter the stent is intended to have when implanted in a body. Typically, the process is initiated by providing a tubular element 520 that is coated with a layer of photoresistive material 522. The tubular element 520 is mounted on a rotatable tube holding structure, such as a mandrel, suitable for rotating the tube 520 about its longitudinal axis. A light source 538 provides light 532 having a suitable wavelength for exposing the photoresistive material 522. The light 532 generated by the light source 538 is controlled by an aperture 530 or shutter structure. The light is also controlled by a photographic film tool such as a moveable pattern mask 527 that is positioned between the source of light and the tube 520. The pattern mask 527 has a pattern of apertures through which the light 532 travels to expose the photoresistive material 522 on the tube 520. By coordinating the movement of the pattern mask 527 with the rotation of the tube 520, a specific exposure pattern is created on the tube 520. The exposed pattern is then developed and a chemical etching solution is used to cut the exposed pattern into the tube 520. Finally, any remaining photoresistive material is removed from the tube 520. It will be appreciated that a variety of patterns can be cut into the tube 520. Exemplary patterns include circles, triangles, diamonds, squares, rectangles and hexagons, polygons, serpentine configurations and ovals.

The aforementioned photoresistive layer 522 typically includes positive or negative photoresistive polymers commonly known in the art. Some positive photoresistive polymers that may be used are Novolak® based materials such as Photoposit® 111 Photo Resist, Photoposit® 119 S Photo Resist and Photoposit® SP 20-29 Photo Resist, all available from Shipley Company, Inc., 500 Nickerson Road, Marlborough, Mass. 01752. Some negative photoresistive polymers that may be used are KTFR Negative Photoresist, from KTI Chemicals Incorporated, 2 Barnes Industrial Park Road, Wallingford, Conn. 06492. These positive or negative photoresistive polymers are applied to the tube 520 by techniques such as spraying, vapor deposition, or dip coating, as well as other conventional coating techniques known in the art.

The light 532 from the light source 538 is preferably caluminated and of a wavelength between approximately 200–550 nm, but may be varied depending on the particular photoresistive material employed.

It will be appreciated that the above described acid etching technique is but one example of many cutting techniques that can be used to pattern the tube 520. Additional methods for cutting a tube include electrical discharge machining (EDM), laser cutting and stamping.

It will be appreciated that a variety of stent configurations could be suitably used in accordance with the principles of the present invention. Important considerations in designing a stent include the collapsibility of the stent, the reinforcement strength of the stent, and the flexibility of the stent.

Figure 7:
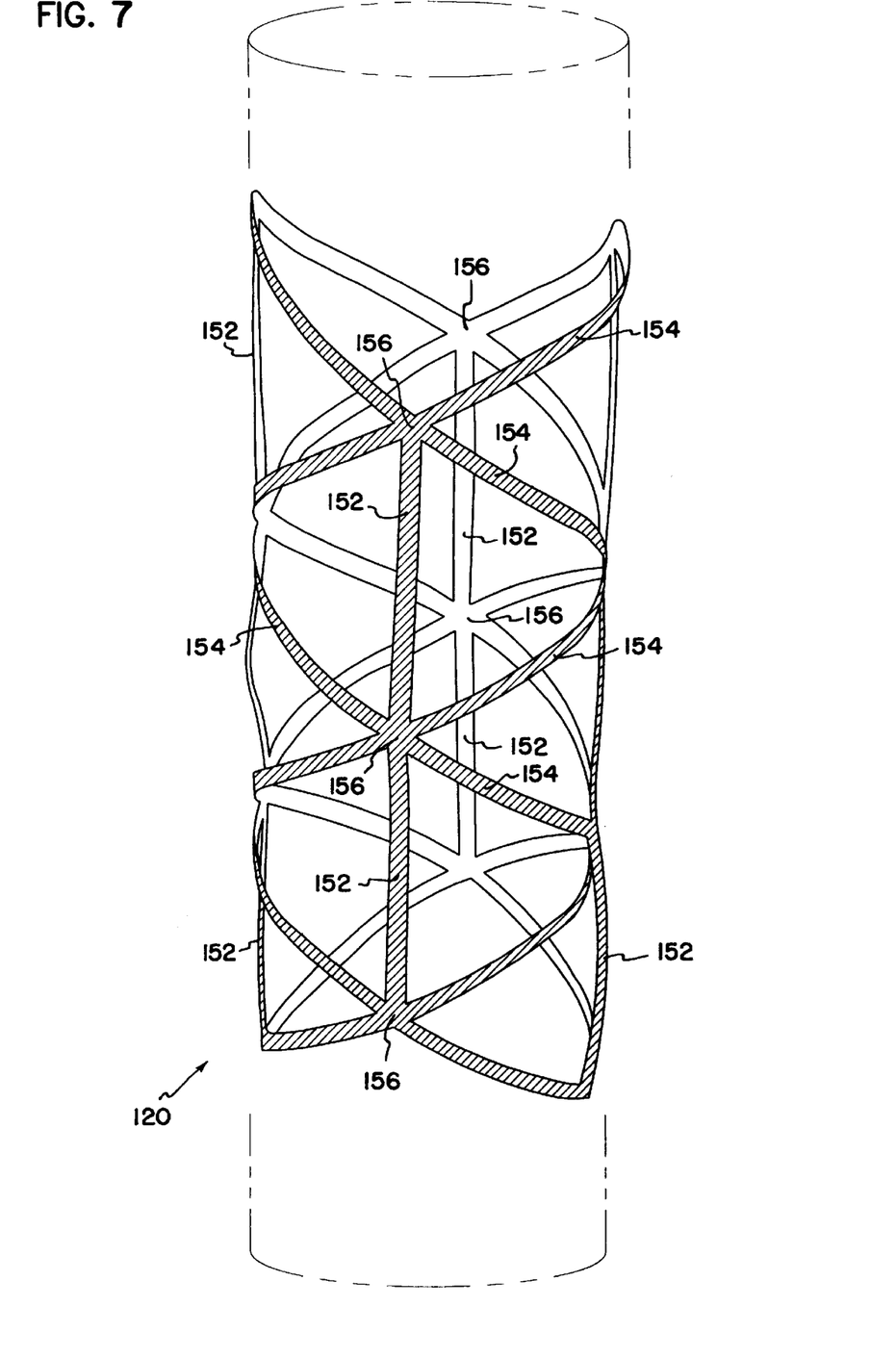
FIG. 7 shows a stent having triangular openings cut therein.

FIG. 7 shows a stent 120 comprising an elongated tube member having a plurality of triangular openings 150 cut therein. The triangular openings 150 are defined by a plurality of longitudinal struts 152 and radial struts 154 that are interconnected at node points 156. Two longitudinal struts 152 and four radial struts 154 are connected at each node point 156.

Figure 8:
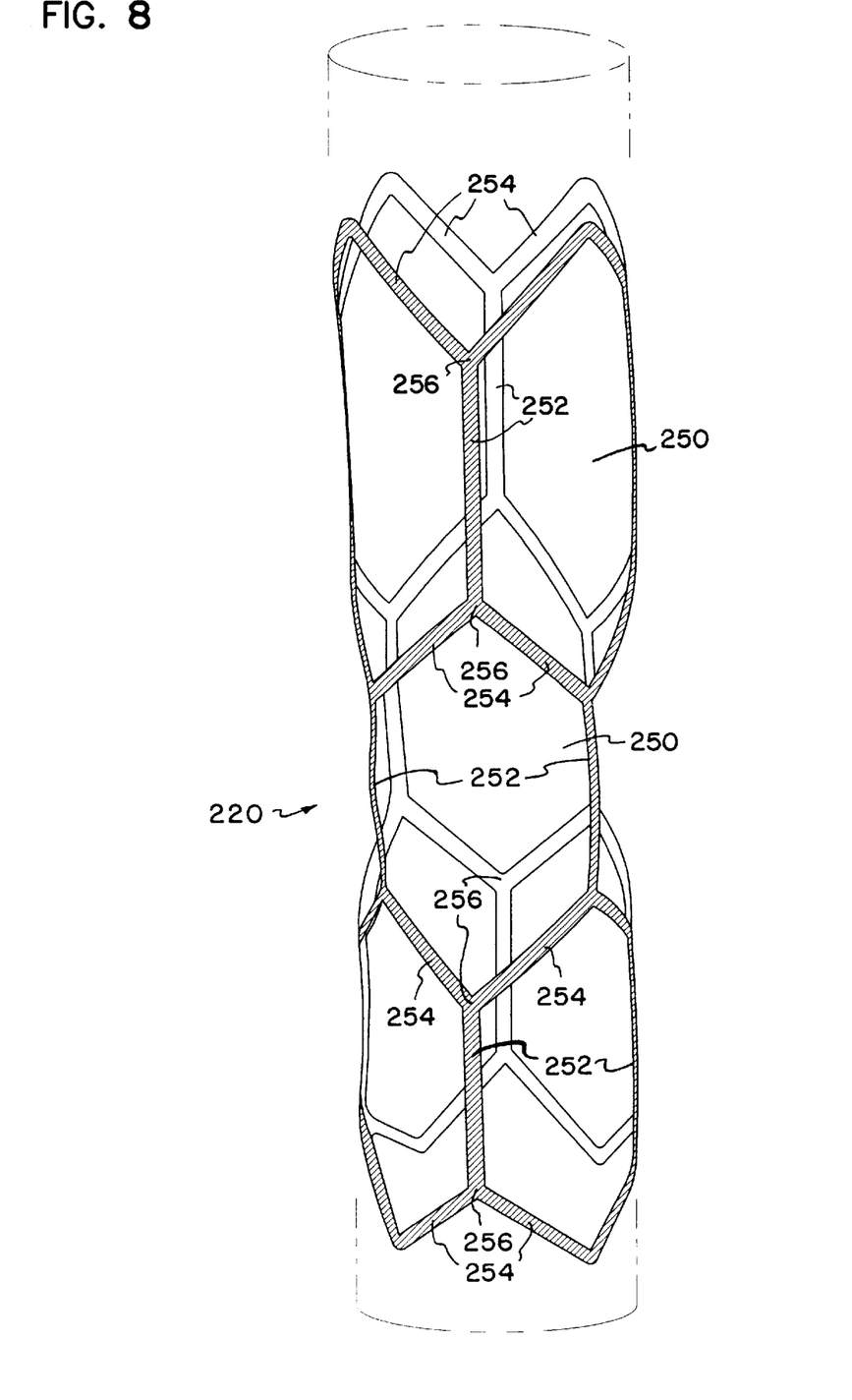
FIG. 8 shows a stent having hexagonal openings cut therein.

FIG. 8 shows a stent 220 comprising an elongated tube member having a plurality of hexagonal openings 250 cut therein. The hexagonal openings 250 are defined by a plurality of longitudinal struts 252 and radial struts 254 that are interconnected at node points 256. One longitudinal strut 252 and two radial struts 254 are connected at each node point 256.

Figure 9:
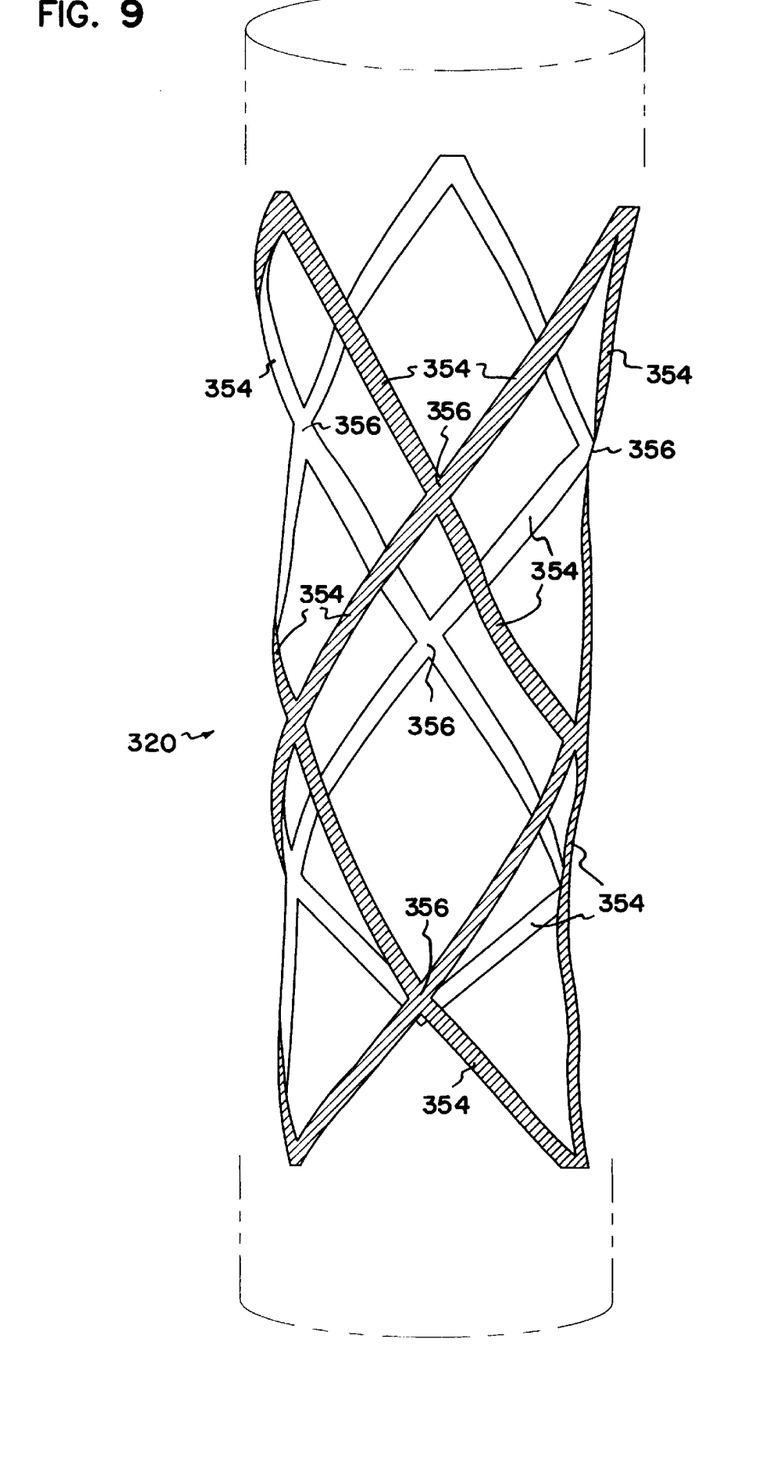
FIG. 9 shows a stent having diamond-shaped openings.

FIG. 9 shows a stent 320 comprising an elongated tube member having a plurality of diamond-shaped openings 350 cut therein. The diamond-shaped openings 350 are defined by a plurality of radial struts 354 that are interconnected at node points 356. Four radial struts 254 are connected at each node point 256.

Figure 10:
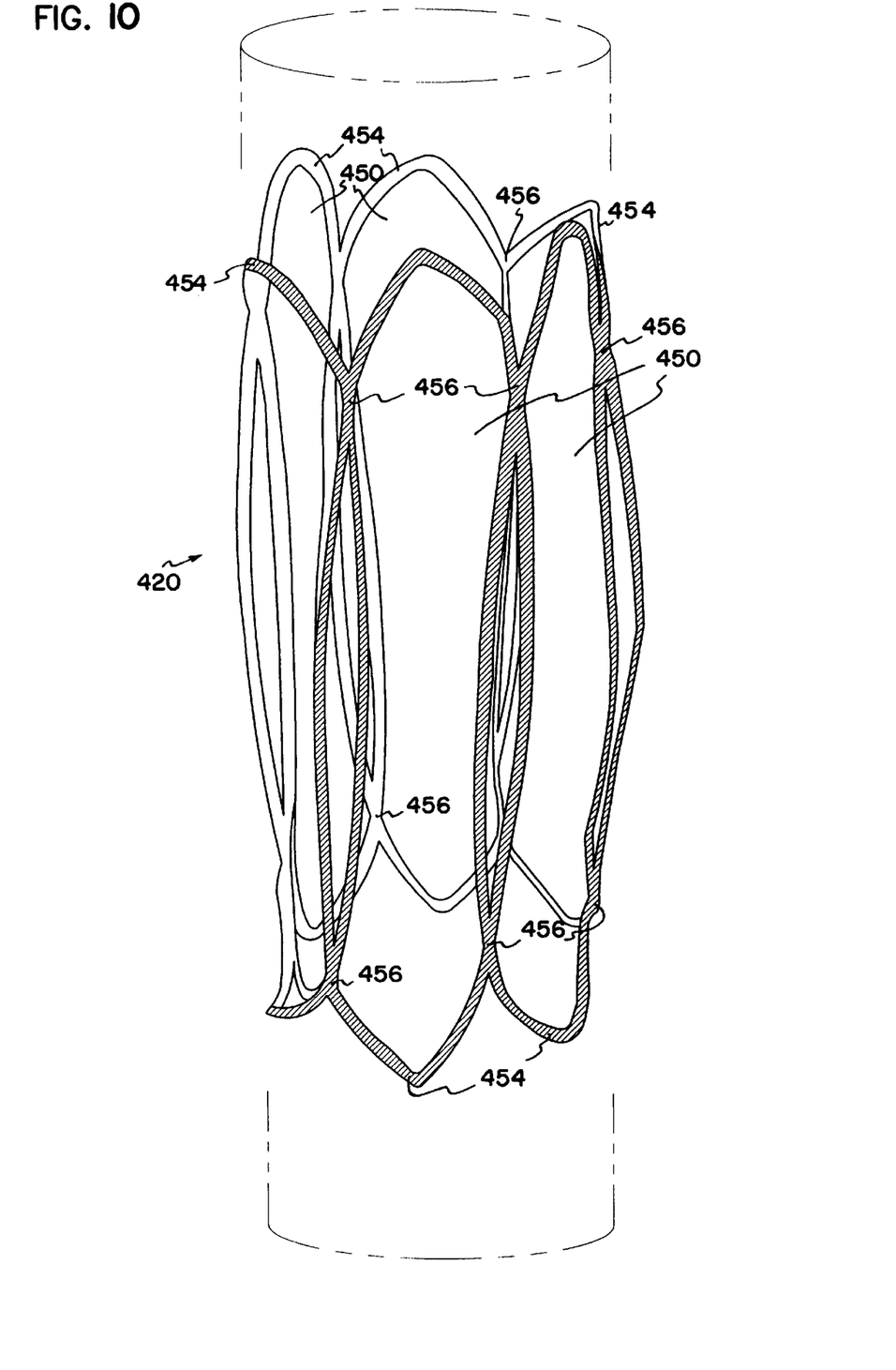
FIG. 10 shows a stent including a plurality of intersecting elongated loop members.

FIG. 10 shows a stent 420 comprising an elongated tube member formed by a plurality of elongated loop members 454 each defining a generally oval shaped opening 450. The loop members 454 intersect one another and are interconnected at node points 456.

The collapsibility of any of the above described stents can be improved by radiusing or curving the intersections between struts at the nodes. Furthermore, by varying the number of radial struts intersecting at each node or by varying the angle between each strut at the node, a stent can be designed having predetermined flexibility, reinforcement strength, and collapsibility characteristics.

It will be appreciated that in each of the aforementioned stent embodiments, it is preferred for all of the struts to have axial components that are substantially parallel to the longitudinal axes of the stents. In other words, it is preferred for none of the struts to be aligned within planes that are perpendicular to the longitudinal axes of the stents. The axial arrangement of the struts is significant because it facilitates collapsing the stents from the expanded orientations to the collapsed orientations. Struts aligned within planes perpendicular to the longitudinal axes of the stents have a tendency to buckle or kink thereby interfering with the collapsibility of the stents. Also, it is significant that each of the aforementioned stent designs is preferably manufactured by cutting apertures within a solid tube while the tube is in an expanded orientation. Consequently, unlike stents manufactured by wrapping wire about a mandrel, the above described stents have struts that are non-overlapping/non-intertwined when in the expanded configuration and that are uniformly aligned within cylinders defined by the stents. It will be appreciated that when such stents are collapsed, there may be some overlapping of the strut members. Also, it will be appreciated that the broad scope of the present invention includes stents having overlapping/intertwined members.

Although it is preferred for all of the stent struts to have axial components that are substantially parallel to the longitudinal axes of the stents, such an alignment is not required. Certain stent embodiments may include struts aligned perpendicularly with respect to the longitudinal axes of the stents so as to maximize the reinforcing strength provided by the stents.

With regard to the foregoing description, it is to be understood that changes may be made in detail, especially in matters of the construction materials employed and the shape, size, and arrangement of the parts without departing from the scope of the present invention. It is intended that the specification and depicted embodiment be considered exemplary only, with a true scope and spirit of the invention being indicated by the broad meaning of the following claims.

What is claimed is as follows:

1. A method for collapsing a stent comprising:
   providing a stent having an expanded orientation;
   placing a catheter balloon within the stent;
   applying centripetally directed radial forces substantially uniformly about a perimeter of the stent, the radial forces being of sufficient magnitude to deform portions of the stent beyond the elastic limits of the portions such that the stent collapses radially inward from the expanded orientation to a collapsed orientation in which the stent is compressed upon the balloon and sized for insertion within a body passageway.

2. The method of claim 1, wherein the radial forces are generated by forcing the stent longitudinally through a tube having a tapered inner diameter.

3. The method of claim 1, wherein the radial forces are generated by an inflatable cuff.

4. The method of claim 1, wherein the radial forces are generated by a mechanical compression apparatus.

5. The method of claim 4, wherein the mechanical compression apparatus comprises a sleeve defining a longitudinal inner opening configured for receiving the stent, the sleeve being moveable between a first position in which the inner opening is expanded, and a second position in which the inner opening is constricted.

6. The method of claim 1, further comprising partially pre-collapsing the stent prior to inserting the balloon within the stent.

* * * * *